(12) United States Patent
Lakowicz et al.

(10) Patent No.: US 7,400,397 B2
(45) Date of Patent: Jul. 15, 2008

(54) OPTICAL STRUCTURES FOR METAL-ENHANCED SENSING

(75) Inventors: Joseph Lakowicz, Ellicott City, MD (US); Zygmunt Gryczynski, Ellicott City, MD (US); Chris Geddes, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 11/488,001

(22) Filed: Jul. 18, 2006

(65) Prior Publication Data
US 2006/0256331 A1   Nov. 16, 2006

Related U.S. Application Data

(62) Division of application No. 10/633,715, filed on Aug. 5, 2003, now Pat. No. 7,095,502.

(60) Provisional application No. 60/401,459, filed on Aug. 6, 2002, provisional application No. 60/401,460, filed on Aug. 6, 2002.

(51) Int. Cl.
*G01J 3/30* (2006.01)
(52) U.S. Cl. .......................... 356/317; 356/445; 385/12
(58) Field of Classification Search ................ 356/317, 356/445; 385/12
See application file for complete search history.

(56) References Cited

U.S. PATENT DOCUMENTS

| | | | |
|---|---|---|---|
| 4,649,280 A * | 3/1987 | Holland et al. ............ 250/483.1 |
| 4,844,869 A | 7/1989 | Glass | |
| 5,359,681 A | 10/1994 | Jorgenson et al. | |
| 5,485,277 A | 1/1996 | Foster | |
| 5,830,766 A * | 11/1998 | Attridge et al. ............. 356/317 |
| 6,272,262 B1 * | 8/2001 | Kopelman et al. ............ 385/12 |
| 6,361,190 B1 | 3/2002 | McDermott | |
| 6,487,326 B1 * | 11/2002 | Pantano et al. ................ 385/12 |
| 6,558,958 B1 * | 5/2003 | Pilevar et al. ............ 422/82.08 |

FOREIGN PATENT DOCUMENTS

JP              07-07184 A1    1/1995

OTHER PUBLICATIONS

Lakowicz, "Radiative Decay Engineering: Biophysical and Biomedical Applications," *Anal. Biochem.*, vol. 298, (2001), pp. 1-24.
Lakowicz et al., "Radiative Decay Engineering: 2. Effects of Silver Island Films on Fluorescence Intensity, Lifetimes and Resonance Energy Transfer," *Anal. Biochem.*, vol. 301, (2002), pp. 261-277.

* cited by examiner

*Primary Examiner*—Kara E Geisel
(74) *Attorney, Agent, or Firm*—Sughrue Mion, PLLC

(57) ABSTRACT

The present invention is directed to optical structures and methods detecting the fluorescence of a molecule using metal-enhanced fluorescence. In particular, the invention describes the use of surface plasmon excitation for excitation of fluorophores near the metal surface and the efficient collection of the emission by coupling into the plasmon resonance and directing towards the detector. More particularly, the present invention makes use of the unique directionality of the plasmon induced fluorescence signal. The present invention is directed to optical structures using metal enhanced fluorescence including: an optical fiber having a conductive external coating; a light emitting diode (LED) having a conical shaped depression with curved sides on a front end surface, the curved sides having a conducting coating on the outer surface with respect to the LED.

11 Claims, 12 Drawing Sheets

Fibre-optics for Use in Metal-enhanced Fluorescence Sensing

Fibre-optics for Use in Metal-enhanced Fluorescence Sensing

Fibre-optics for Use in Metal-enhanced Fluorescence Sensing

Fibre-optics for Use in Metal-enhanced Fluorescence Sensing

Fibre-optics for Use in Metal-enhanced Fluorescence Sensing

Optical Structures for Metal Enhanced Fluorescence Sensing

Modified LED Surface or Disposable Cartridge that Goes Over the Top of a Light Source or Even Ambient Light Applications
Resonance Energy Transfer Immunoassays on the Surface on the Modified LED

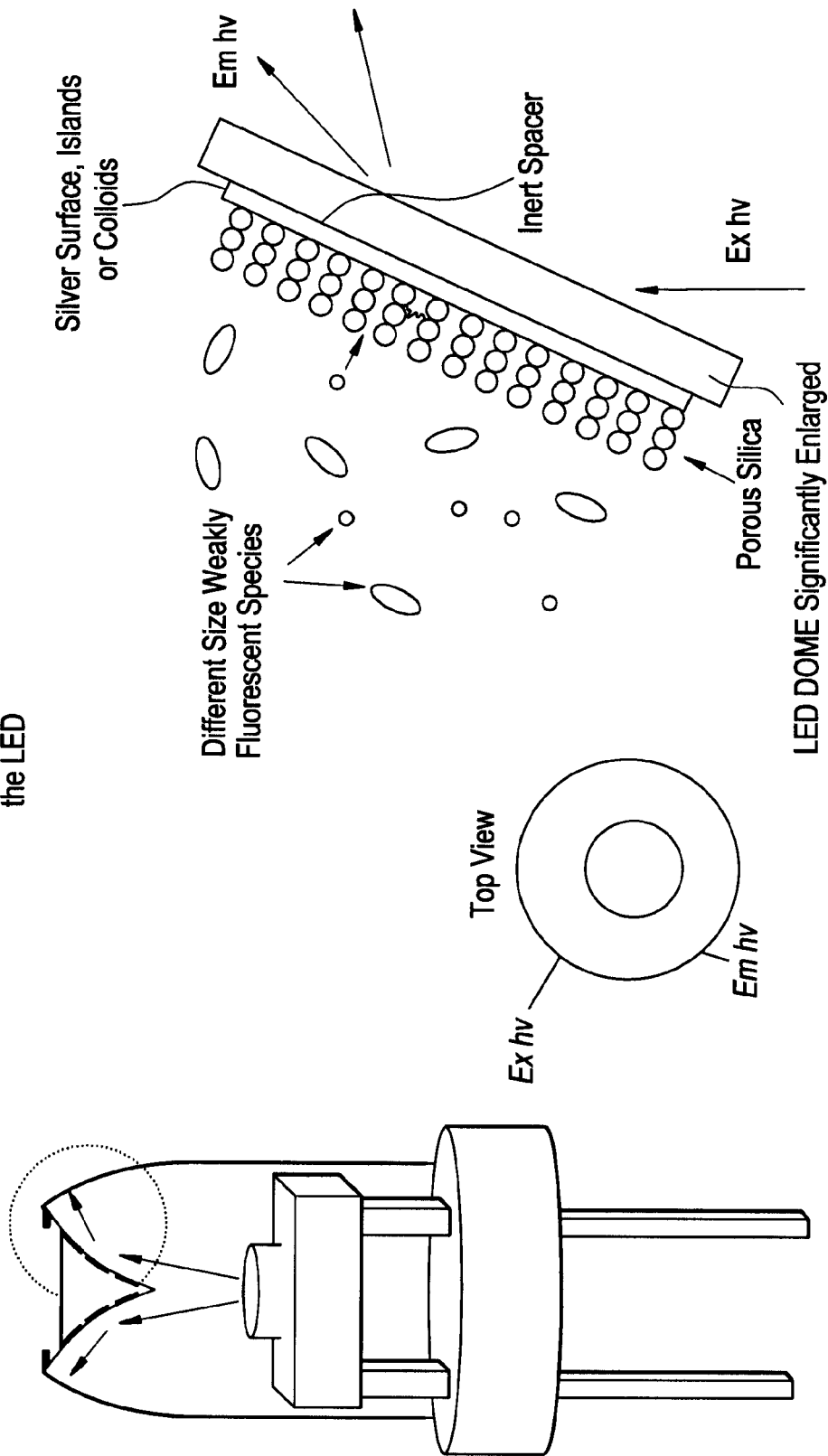

OPTICAL STRUCTURES FOR METAL-ENHANCED SENSING

This is a divisional of application Ser. No. 10/633,715 filed Aug. 5, 2003, now U.S. Pat. No. 7,095,502 which claims benefit of Provisional Application No. 60/401,459 filed Aug. 6, 2002, and Provisional Application No. 60/401,460 filed Aug. 6, 2002. The entire disclosures of the prior applications, application Ser. No. 10/633,715 is hereby incorporated by reference.

This is a Utility Application that claims benefit of Provisional Application Nos. 60/401,459 and 60/401,460, both accorded a filing date of Aug. 6, 2002, the disclosures of which are incorporated herein by reference.

The work leading to this invention was supported in part by the U.S. Government under grant number RR-08119 awarded by the NIH National Center for Research Resources. The U.S. Government has certain rights in this invention.

BACKGROUND OF THE INVENTION

1. Field of the Invention

This is a Utility Application that claims benefit of Provisional Application Nos. 60/401,459 and 60/401,460, both accorded a filing date of Aug. 6, 2002, the disclosures of which are incorporated herein by reference.

The present invention is directed to apparatus and methods for increasing and detecting the fluorescence emitted by a molecule using metal-enhanced fluorescence. In particular, the invention describes the use of surface plasmon excitation for excitation of fluorophores near the metal surface and the efficient collection of the emission by coupling into the plasmon resonance and directing towards the detector. More particularly, the present invention makes use of the unique directionality of the plasmon induced fluorescence signal.

2. Background of the Related Art

Many experiments have been done demonstrating that metal particles can enhance fluorescence. Results in the literature show that fluorescence can be excited via the surface plasmon excitation. See Lakowicz, J. R., *Radiative decay engineering: biophysical and biomedical applications*. Anal Biochem, 2001. 298(1): p. 1-24; Lakowicz, J. R., et al., *Radiative decay engineering: 2. Effects of Silver Island films on fluorescence intensity, lifetimes, and resonance energy transfer*. Anal Biochem, 2002. 301(2): p. 261-77. Results in other publications have shown that emission can couple back into the plasmon at discrete angles.

FIG. 1 shows the well-known total internal reflection in fibers, where the refractive index n2>n1. Light approaching the refractive index boundary from the medium of higher refractive index is reflected away from the normal. For small angles of incidence, there is both a reflected ray and a refracted ray. However at some critical angle of incidence, θc, the refracted ray emerges parallel to the surface. For any angle of incidence greater than θc the light is totally internally reflected back into the medium of higher refractive index.

Fluorescent effects can be excited using various light sources. One light source is Xenon arc lamp. However, the spectral characteristics of the lamp vary over time and cannot provide a stable output. Light-Emitting-Diodes (LED) sources are also used. The LED sources can provide a stable output and offer opportunities for miniaturization and tunability of the output wavelength.

SUMMARY OF THE INVENTION

The present invention provides optical structures for metal-enhanced fluorescence sensing. One embodiment comprises an optical fiber having a conductive external coating, such as silver. The highly conductive coating providing a sensing surface, which senses fluorophores disposed in close proximity to said sensing surface. The structure also includes a detector, wherein fluorescence emissions of the fluorophores are coupled back into the highly conductive coating so that the fluorescence emissions exit the coating at a plasmon angle into the optical fiber. Further, the fluorescence emissions coupled into the optical fiber are totally internally reflected within the optical fiber in a direction towards the detector, which detects the fluorescence emissions.

The present invention further provides a method of metal-enhanced fluorescence sensing, comprising applying a highly conductive coating to a surface of an optical fiber, and introducing a solution containing analytes to the highly conductive coating; employing surface plasmon excitation to cause an excitation of fluorophores adjacent to a highly conductive coating on an optical fiber; coupling the fluorescence emissions of the fluorophores into the highly conducting coating so that the fluorescence emissions exit the highly conducting coating at the plasmon angle into the optical fiber, wherein the fluorescence emissions being totally internally reflected within the fiber in a direction towards a detector.

The present invention further provides a sensor using metal enhanced fluorescence, comprising a light emitting diode (LED) having a conical shaped depression on a front end surface. The conical shaped depression having curved sides, where the curved sides have a highly conductive coating on an outer surface of the LED. The radius of curvature of the curved sides is set to provide directional emissions. The directional emissions are induced by a surface plasmon excitation of a fluorophore disposed in close proximity to the highly conducting coating.

Further, the invention includes a method of detection that includes forming a front end surface of a light emitting diode (LED) to have a conical shaped depression with the conical shaped depression having a curved side; setting a radius of curvature of the curved sides to provide directional emissions; coating on an outer surface of the curved side with a highly conductive material; inducing directional emission by surface plasmon excitation of a fluorophore disposed in close proximity to the highly conducting material.

BRIEF DESCRIPTION OF THE DRAWINGS

Preferred embodiments of the invention are described in detail below in conjunction with the attached drawings in which:

FIG. 12 is an illustration of size inclusion/exclusion sensing on the surface of the LED.

DETAILED DESCRIPTION OF THE INVENTION

The present invention makes use of the unique directionality of the plasmon induced fluorescence signal. Typically fluorophores in solution emit isotropically into the solution. However, if the fluorophore is close to a semi-transparent metallic surface, metallic islands or colloids, then fluorescence emission can be coupled into the metal and become directional rather than isotropic. Under suitable conditions, as much as 85% of the emission is thought to be able to couple back into the metal and exit at the plasmon angle.

First Embodiment

The first embodiment is directed to compositions and methods for increasing, and detecting the fluorescence of a molecule, in particular, compositions and methods for excitation of fluorophores and detection of fluorophore emission. Though this embodiment is described relative to fluorophore emission detection, the invention is equally applicable to detection of chromophore emissions, lumophore emissions and other light emitting species, such as metal-ligand complexes.

Figure 1:
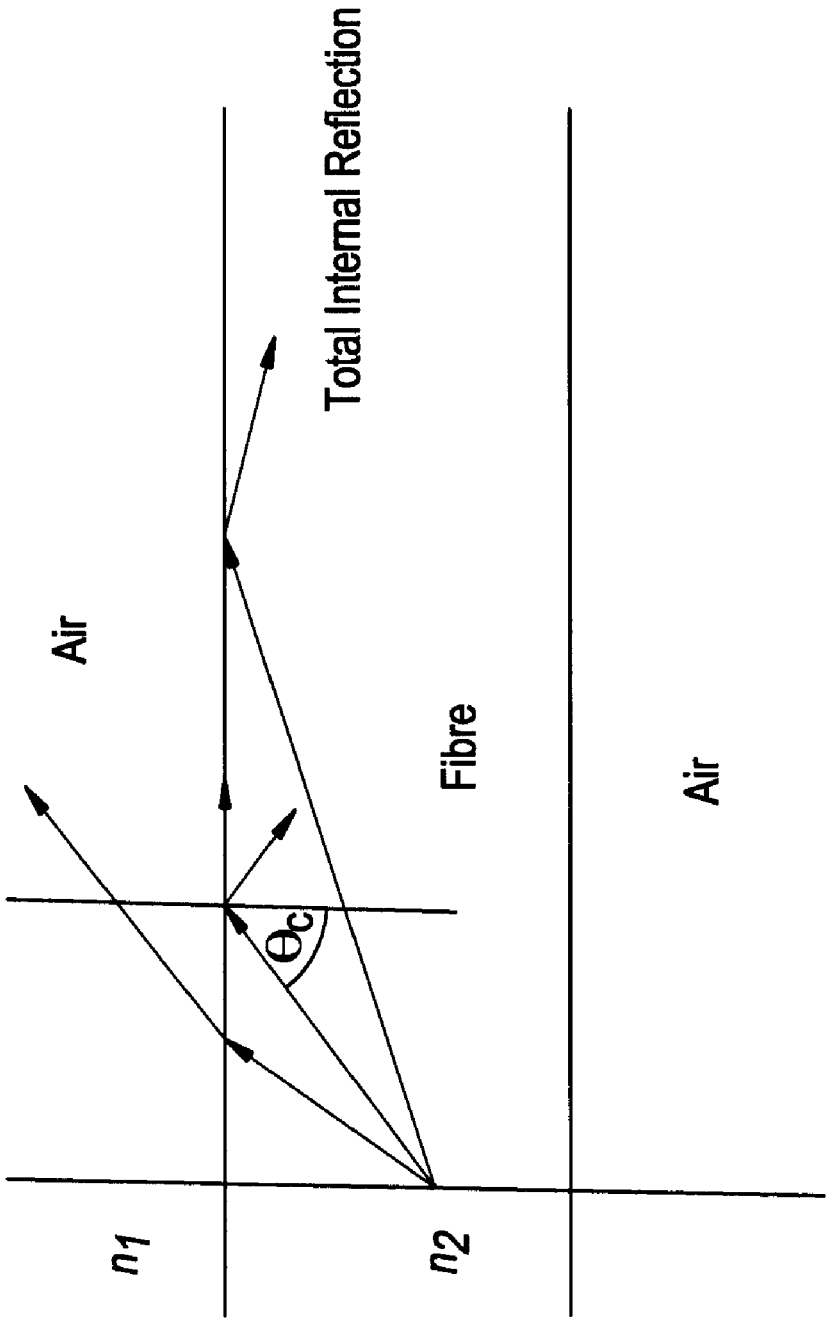
FIG. 1 is an illustration of internal reflection in fibers, where the refractive index n2>n1.
Figure 2:
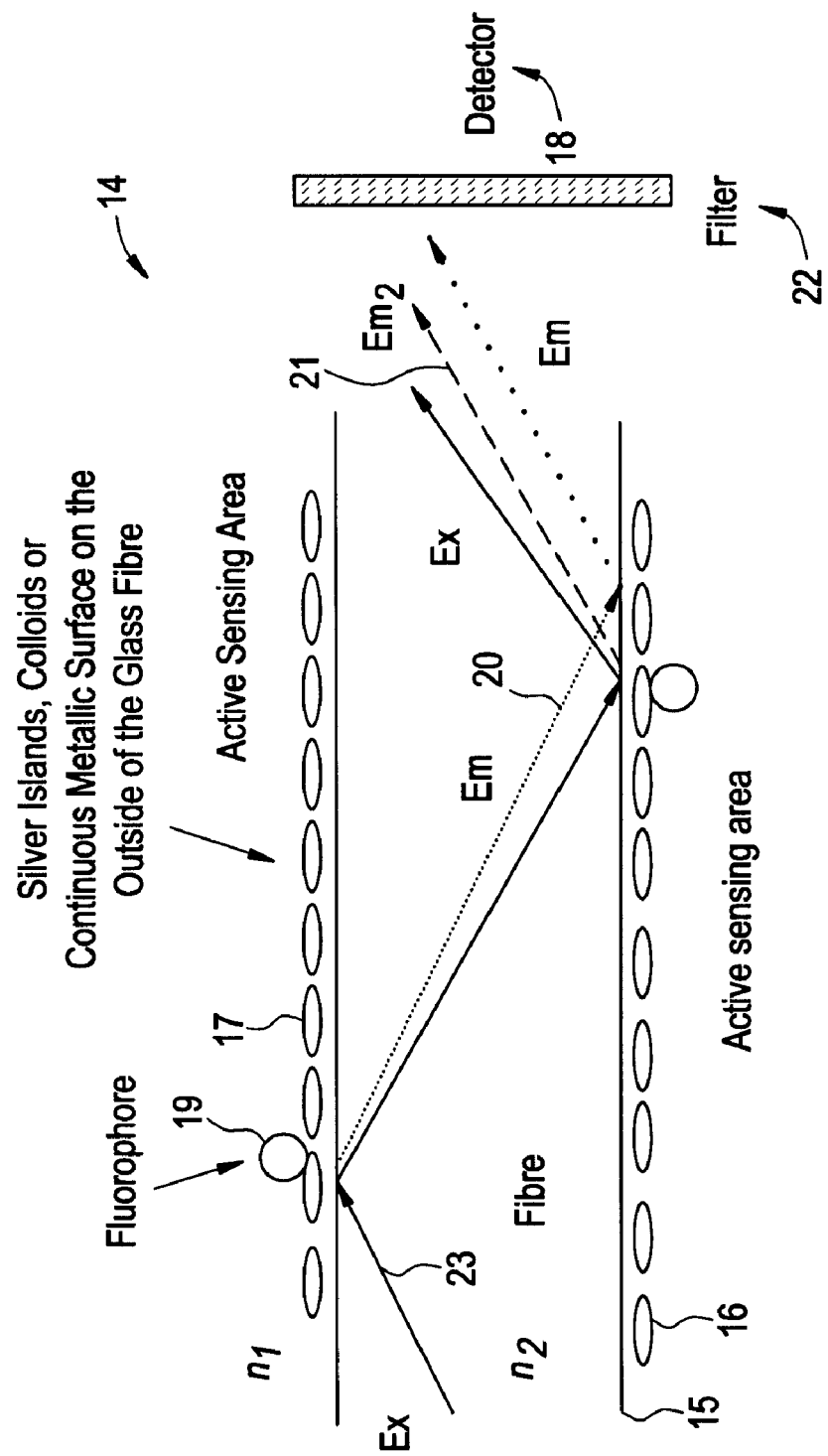
FIG. 2 is an illustration of fiber-optics for use in metal enhanced fluorescence sensing according to an embodiment of the invention.

FIG. 2 illustrates the optical structure for metal-enhanced fluorescence sensing according to this embodiment. This optical structure 14 includes an optical fiber 15, which may comprise a single core or a multi-core structure. The optical fiber has an external highly conducting coating 16, such as silver. The coating may take the form of silver islands, colloids, or continuous metallic surface on the outside of the optical fiber. The metallic element may include any form of noble metals such as silver, gold, platinum and copper.

Through embodiments of the present invention, it was observed that continuous films formed as a semi-transparent metal provided directional fluorophore emissions through the fiber rather than isotropic patterns. Continuous films having a sub-wavelength thickness in comparison with the stimulating light provided directional effects. Films as thick as 200 nm could be used to provide directivity. Improved directionality with a continuous metallic film was observed with thicknesses of approximately 50 nm in the case of a silver or gold conductor.

The emissions were enhanced when the film was not continuous but rather formed with metallic islands. The present invention provided enhanced emissions using islands of elliptical, spherical, triangular or rod-like forms. In exemplary cases, the elliptical islands had aspect ratios of 3/2, and the spherical colloids had diameters of 20-60 nm. However, the invention is not limited to any particular geometry. The most suitable geometry for the island forms will depend on the excitation light wavelength. The fiber surfaces were coated with the metal to about 40% mass thickness coverage and an optical density of approximately 0.4. Using known coating techniques, the placement of metallic islands could be controlled precisely, as close as 50 nm apart.

A solution containing analytes is introduced to the surface area 17 of the optical fiber formed with the highly conducting coating. Emissions from fluorophore activity 19 become totally internally reflected upon application of surface plasmon resonance. Further, a detector 18 detects the Totally Internal Reflected Directional Fluorescence Emission (TIRDFE) within the optical fiber.

Figure 3:
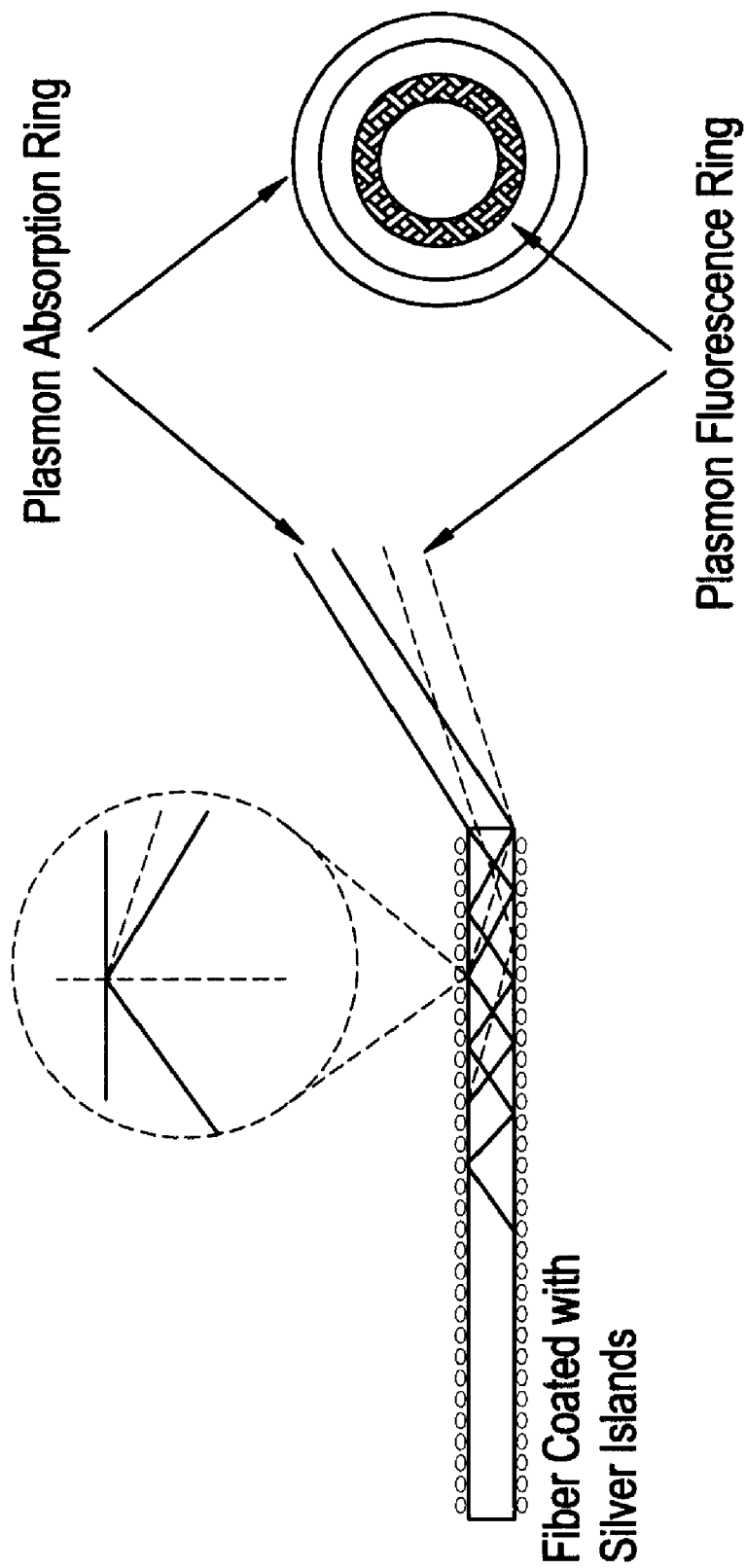
FIG. 3 is an illustration of the separation of the Plasmon Absorption Ring and the Plasmon Fluorescence Ring obtained by the invention.

The invention is an approach to using metal-enhanced fluorescence with fiber optics. In particular, the invention describes how optical fibers can be used with surface plasmon excitation for excitation of fluorophores 19 near the metal surface, and also for efficient collection of the fluorescence emission 20 (Em), 21 (Ex) by coupling into the plasmon resonance and being directed towards the detector 18. FIG. 3 illustrates an end view of the plasmon fluorescence ring (inner ring) caused by total internal reflection of emissions from excitation light. The outer ring of FIG. 3 relates to excitation light. The plasmon angle, the angle at which light couples into the fiber from the metal, will determine the spatial separation between the absorption ring and the fluorescence ring. The plasmon angle, in turn is based on the thickness of the metallic coating and whether formed as continuous film or as islands, the material of the coating, the relative reflective indices n1 and n2, and the wavelength of the excitation light. In the invention, the ratio of the intensities of the inner and outer rings shown in FIG. 3 remains constant for a fixed plasmon angle. Under this situation, any fluorescence measurements obtained can be corrected for light fluctuation or other artifacts. While measurements are shown at an end surface of the fiber in this embodiment, the measurement can also be taken along the length of the fiber.

In the continuous metallic film case, the fluorophore emissions could be detected in the analyte solution up to 500 nm away from the surface of the metal. In the case where the metallic coating is formed by islands, the enhanced fluorophore emissions could be detected in the solution up to 200 nm away from the surface of the metal.

Figure 4:
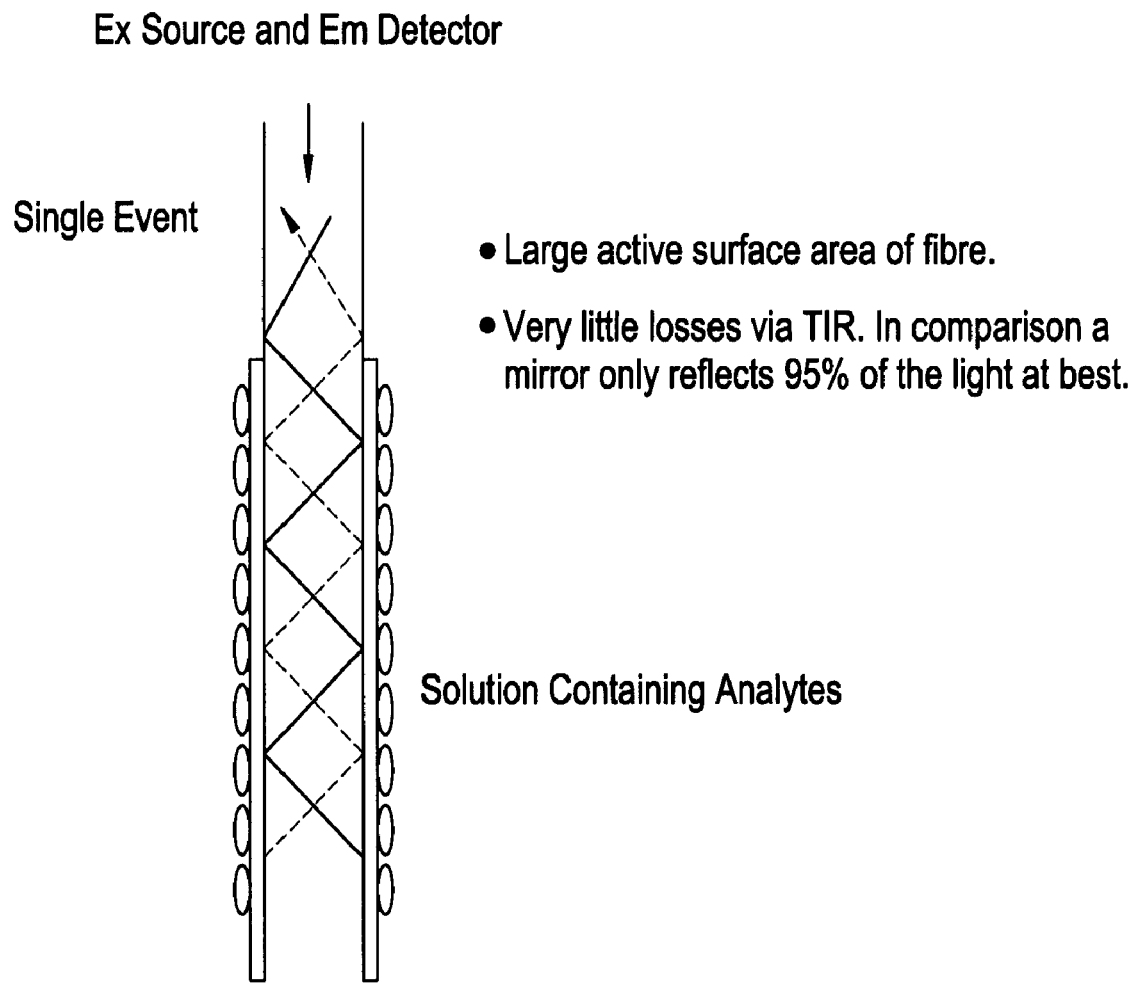
FIG. 4 is another illustration of fiber-optics for use in metal enhanced fluorescence sensing.

The invention makes use of the fact that the fluorescence emission of fluorophores on the surface of a partially or fully silver coated fiber can be made to couple back into the metal at the plasmon angle and be totally internally reflected within the fiber. The large surface of the fiber creates a significantly large active area for sensing opportunities, e.g., immunosensing. The excitation 23 and emission 20, 21 light can be easily distinguished by use of filters 22, as shown in FIG. 2. Further, the excitation and emission light can be reflected back to the detector located with the excitation source, as shown in FIG. 4.

Figure 5:
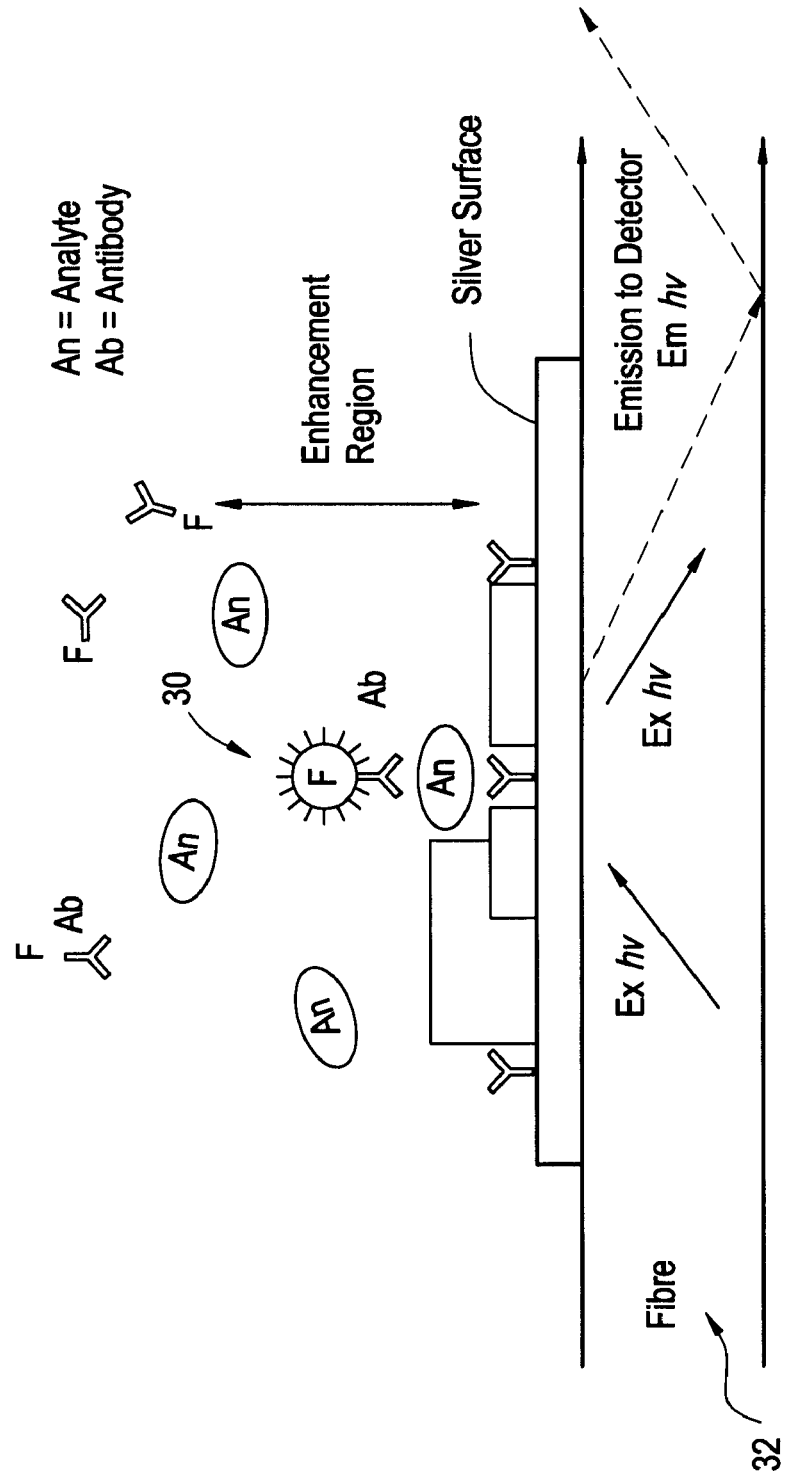
FIG. 5 is an illustration of fluorescence immunoassays with non-fluorescent or fluorescent chromophores on the surface of the fiber according to an embodiment of the invention.

The uses of such a low cost optical-fiber, as a high-surface area highly sensitive sensor, are multifarious. As such, many applications exist in the clinical and analytical sciences as well as in industrial and environmental monitoring. One example is shown in FIG. 5, which illustrates fluorescence immunoassays with fluorescent or non-fluorescent chromophores 30 on a surface 31 of the fiber 32.

Second Embodiment

The second embodiment is an approach to using metal-enhanced fluorescence with simple solid-state light sources. In particular, the invention describes how light emitting diodes (LEDs) can be used with surface plasmon excitation for excitation of fluorophores near the metal surface, and also with efficient collection of the emission by coupling into the plasmon resonance and being directed towards the detector. While a preferred embodiment uses LEDs, this invention could also be used with laser diodes and other incandescent or electroluminescent light sources.

Figure 6:
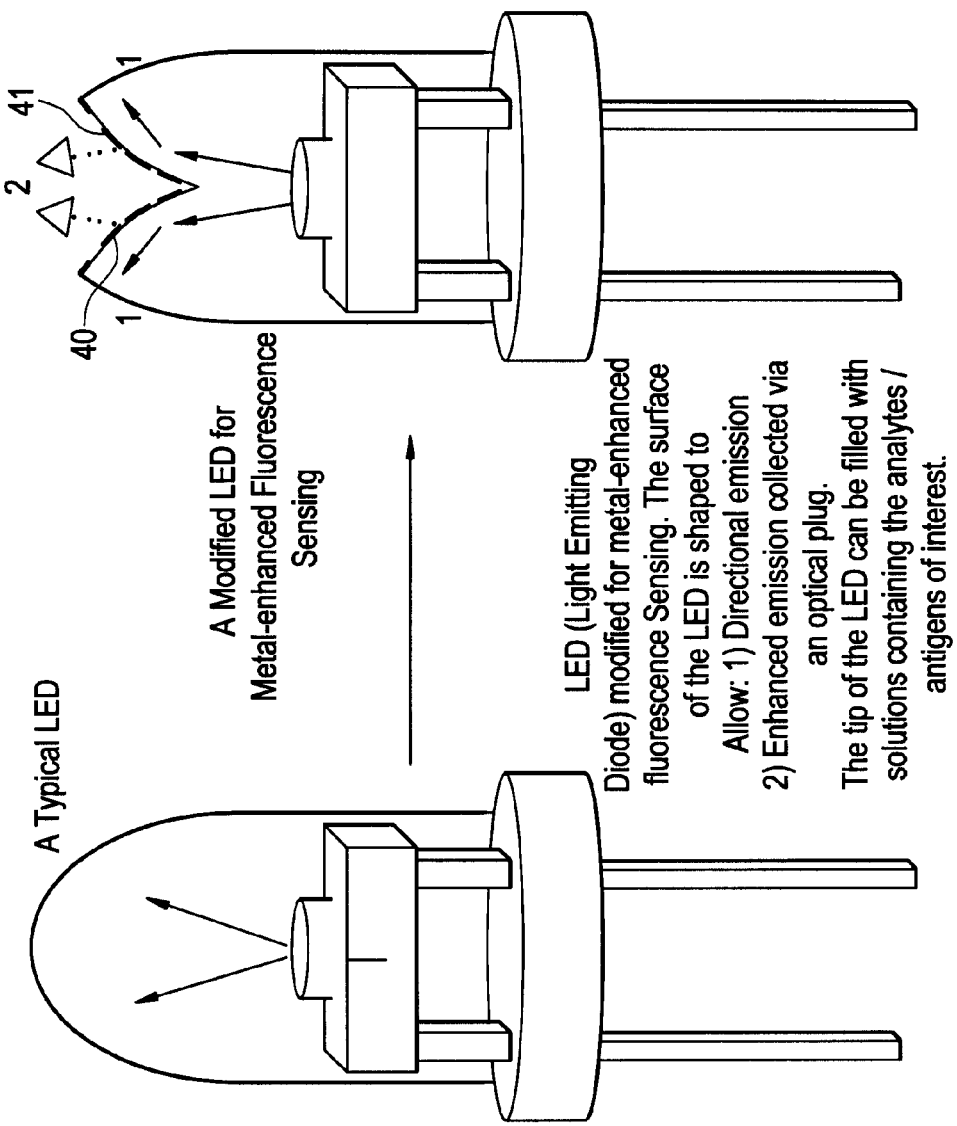
FIG. 6 is an illustration of an optical structure for metal enhanced fluorescence sensing according to an embodiment of the invention.
Figure 7:
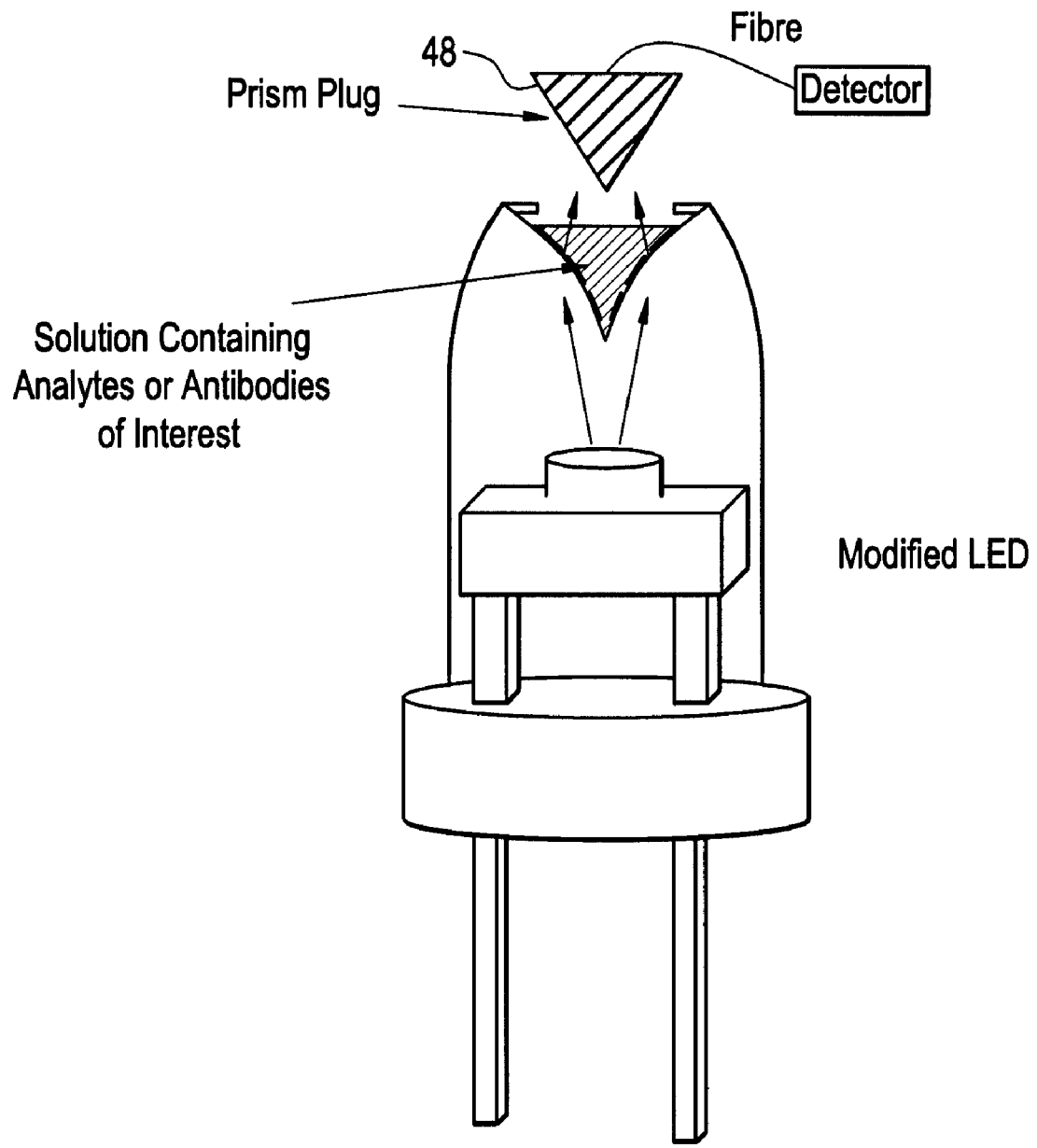
FIG. 7 is another illustration of an optical structure for metal enhanced fluorescence sensing.

FIG. 6 shows one such structure, and how an LED can be modified for both directional emission (1) and for collecting all the fluorescence emission (2) by utilizing an optical plug 48, FIG. 7. The curved structure 40 of the LED is coated with silver islands, colloids or a continuous semi-transparent metallic surface 41 for the enhancement of weakly fluorescent (2) species as well as directional emission (1). The metal islands can be formed internal or external to the LED structure.

Figure 8:
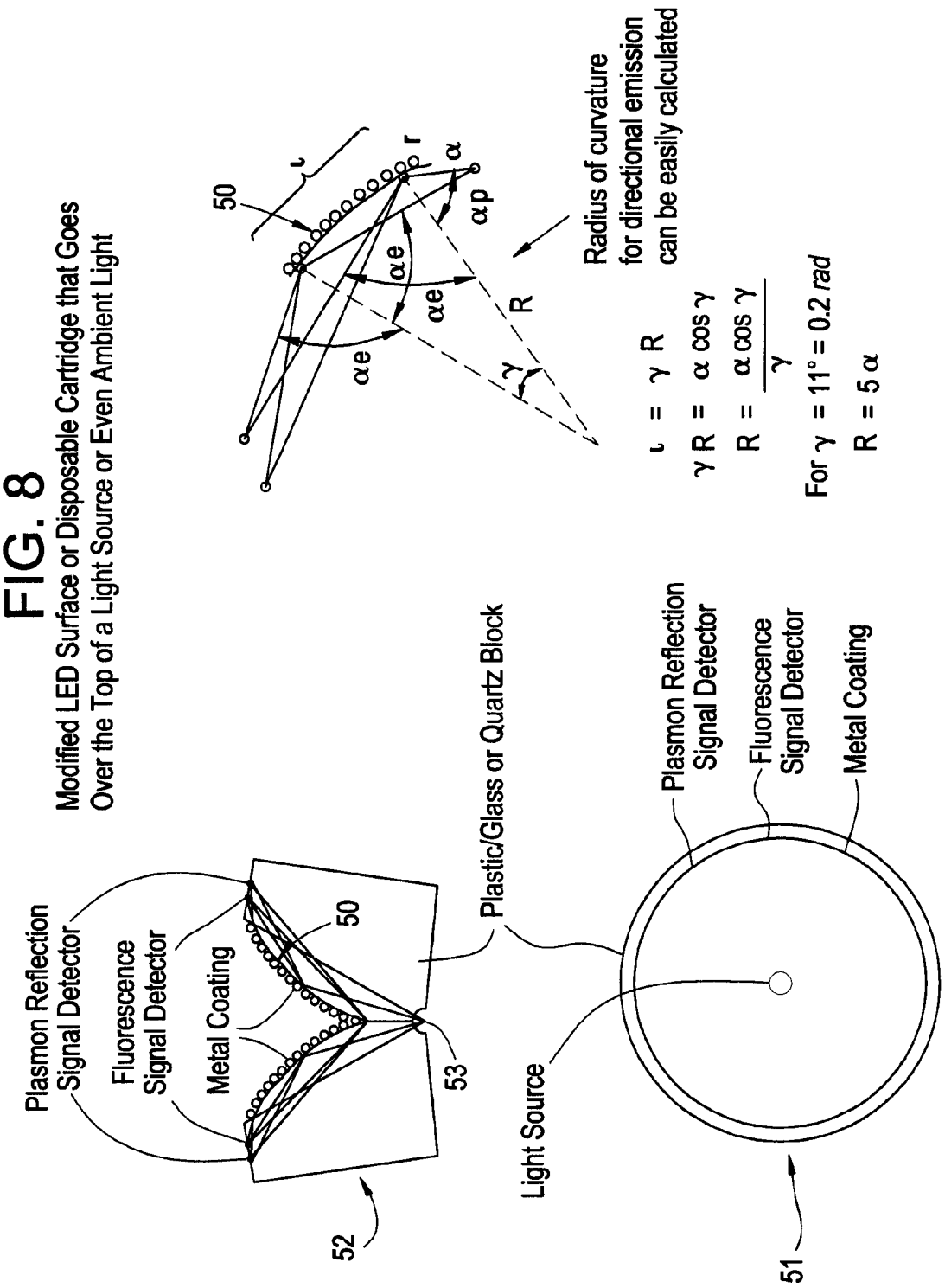
FIG. 8 is an illustration of a modified LED surface or disposable cartridge.
Figure 9:
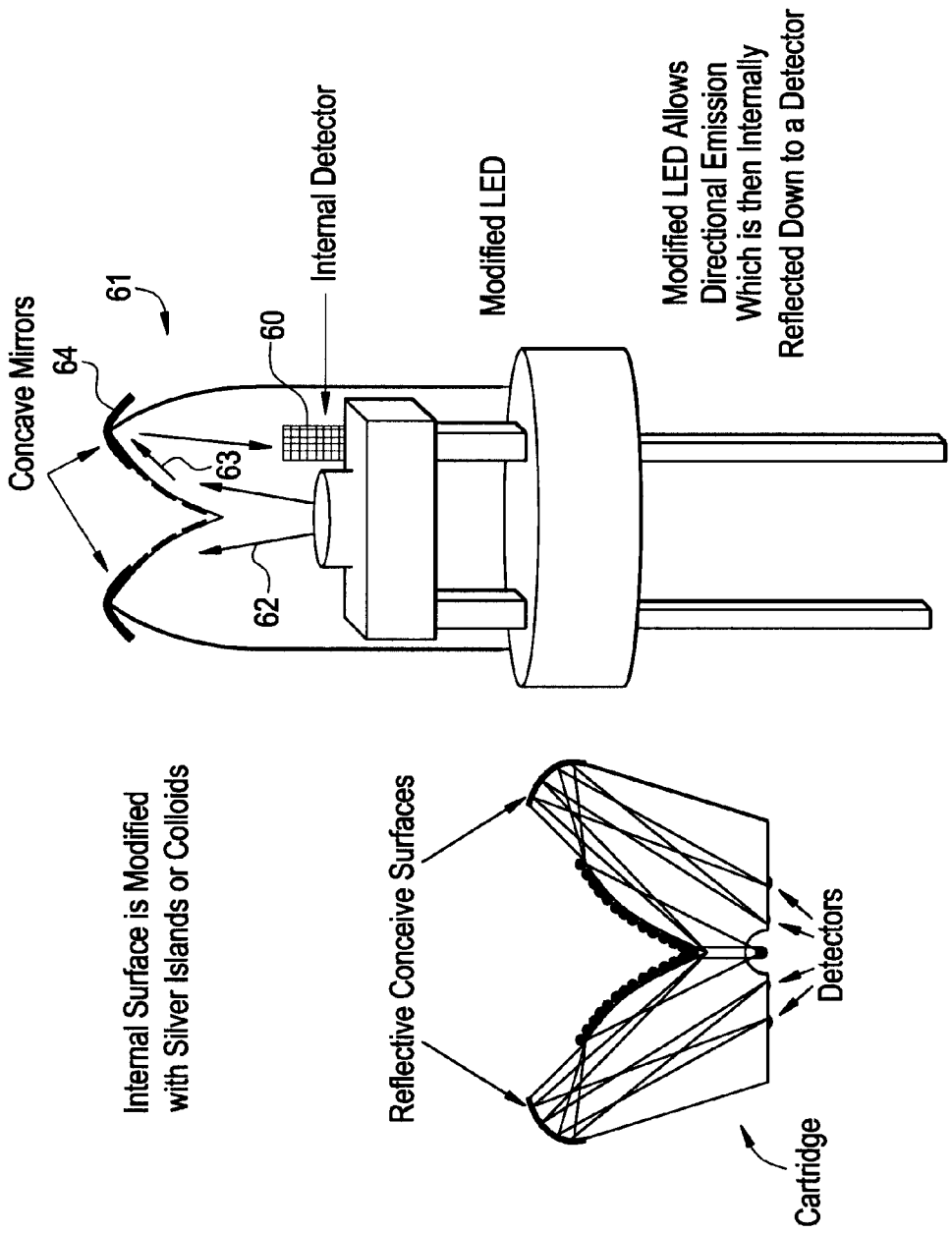
FIG. 9 is another illustration of an optical structure for metal enhanced fluorescence sensing.

FIG. 8 shows that the radius of curvature of the arc 50 formed into the surface of the LED can be readily calculated, which allows for the directional emission to be observed on the surface of the LED. Uniquely, a top view 51 of the LED would show the fluorescence directional emission and the excitation light to be distinctly separated in space, identified by two rings, due to the different excitation reflection and plasmon induced fluorescence emission angles. In a preferred embodiment, a circular detector is used on the top surface of the LED, or the detector 60 is mounted within the LED 61 itself, where the excitation 62 and emission 63 light is reflected back towards the central LED chip by a circular concave mirror 64 as shown in FIG. 9. The appropriate rate of curvature for the LED housing will depend upon the refractive index of the housing, the type of metal coating used, and the wavelength of the excitation light.

The invention comprises modifications to the surface of LEDs for sensing. In a preferred embodiment, the invention also comprises disposable sensor cartridges 52, which are designed and manufactured with a specific geometry to enable directional emission, but can use almost any light source 53, including ambient light as shown in FIG. 8. In a more preferred embodiment, excitation and emission filters are inserted into the sensing cartridges for wavelength discrimination.

Figure 10:
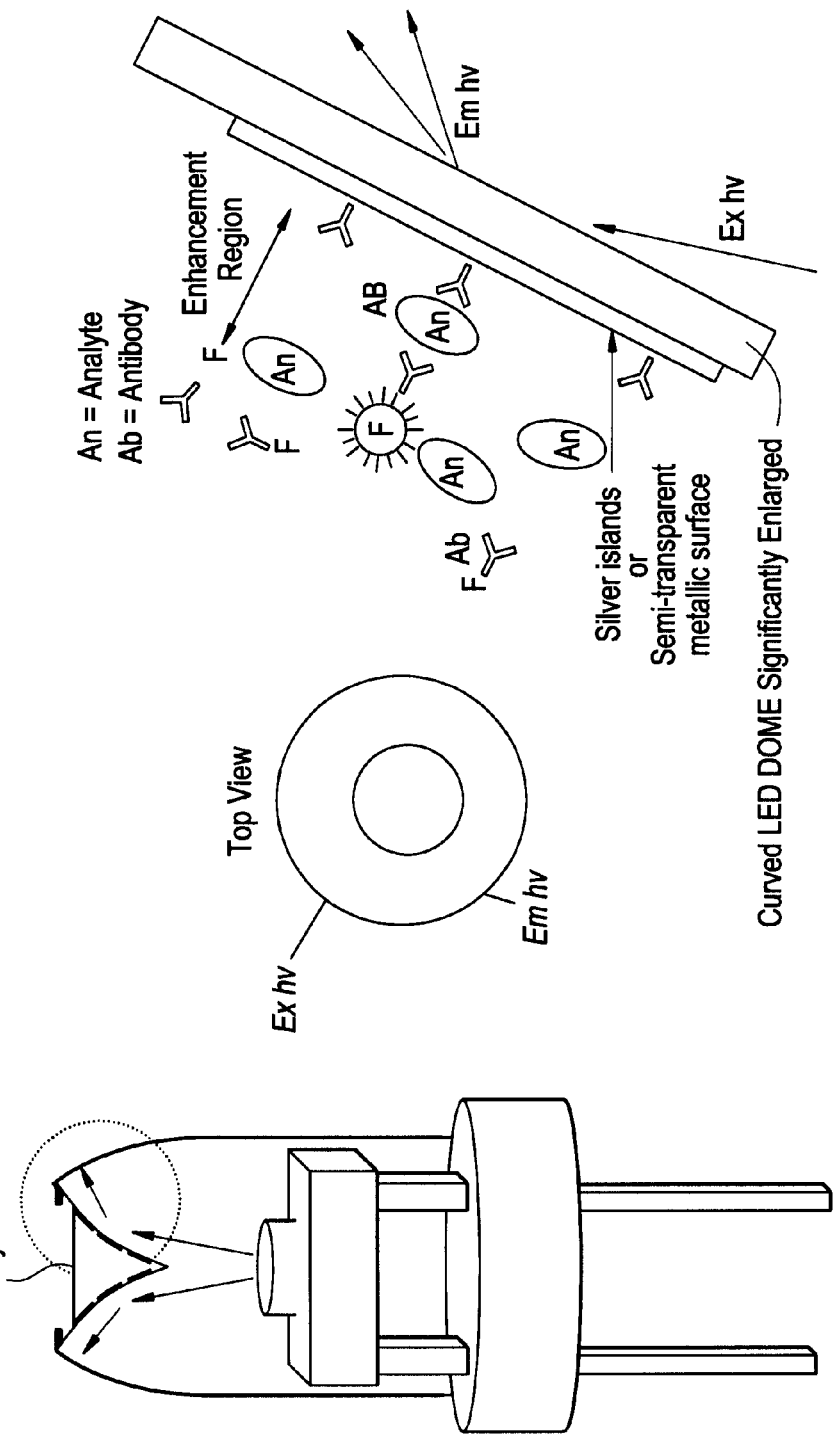
FIG. 10 is an illustration of fluorescence immunoassays with non-fluorescent or fluorescent chromophores on the surface of the LED.
Figure 11:
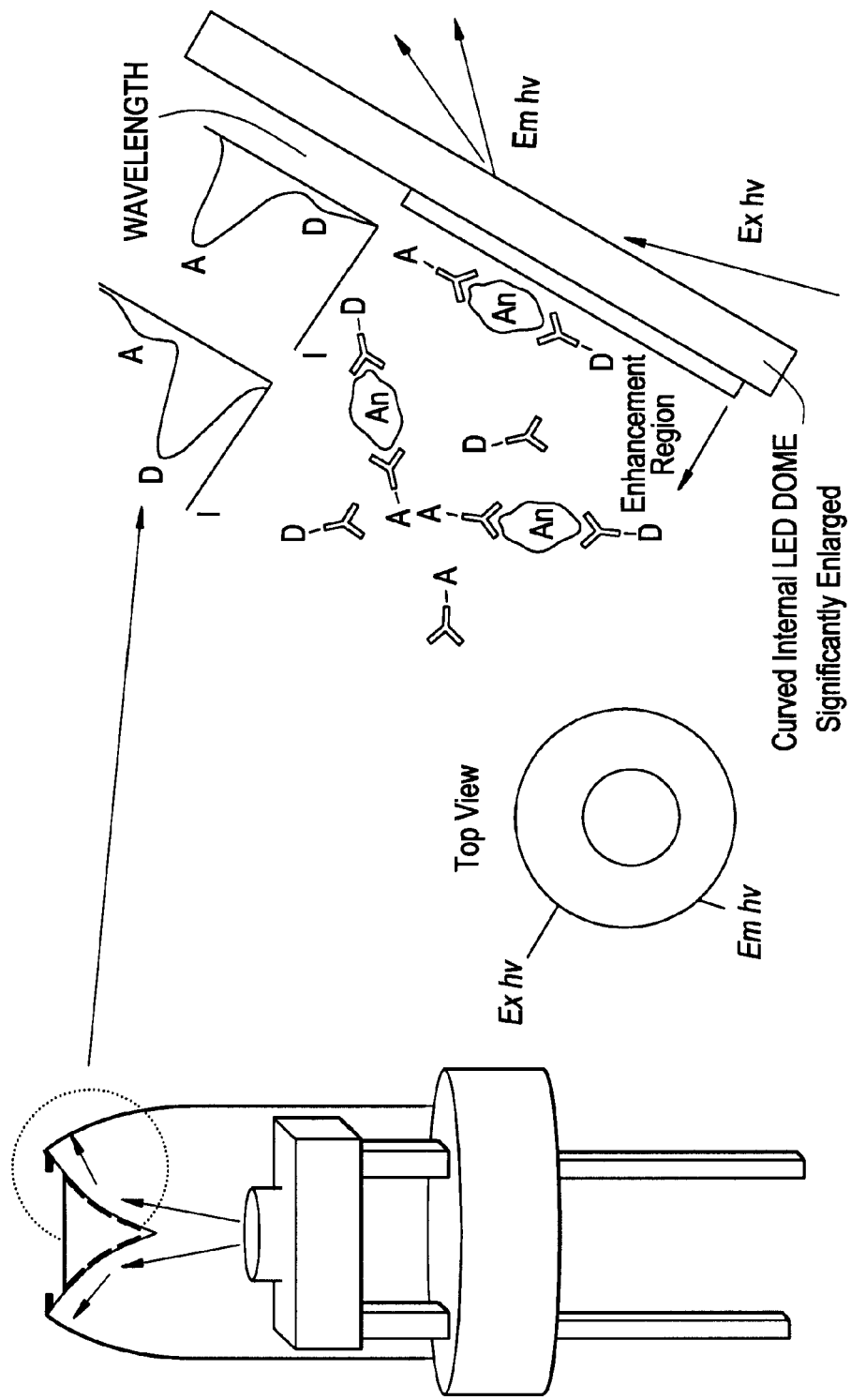
FIG. 11 is an illustration of Resonance Energy Transfer immunoassays on the surface of the modified LED.

The uses of such low cost optical structures as highly sensitive sensors are multifarious. As such, they have useful applications in the clinical and analytical sciences as well as in industrial and environmental monitoring. Such applications include: (1) Fluorescence immunoassays with non-fluorescent or fluorescent chromophores on the surface of the LED, as shown in FIG. 10; (2) Resonance energy transfer immunoassays on the surface of the LED as shown in FIG. 11; (3) Size inclusion/exclusion sensing on the surface of the LED as shown in FIG. 12.

Many companies sell cheap fluorescence excitation sources for multifarious applications. This new source has many advantages for fluorescence, and as such, the potential use of the technology described in this invention to be widespread.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto

What is claimed is:

1. An optical structure for metal-enhanced fluorescence sensing, comprising:
   an optical fiber having a conductive external coating;
   fluorophores disposed adjacent to said conductive external coating, wherein said conductive external coating on said optical fiber comprises colloid spheres;
   a detector disposed at one end of said optical fiber;
   wherein fluorescence emissions of said fluorophores are coupled into said conductive external coating and into said optical fiber via application of surface excitation, and the fluorescence emissions are detected by the detector.

2. An optical structure for metal-enhanced fluorescence sensing according to claim 1, wherein said fluorescence emissions coupled into said optical fiber are totally internally reflected within said optical fiber in a direction towards said detector, which detects said fluorescence emissions.

3. An optical structure for metal-enhanced fluorescence sensing according to claim 1, further comprising:
   a refractive index boundary being a surface of said optical fiber;
   a first and second refractive index on either side of said refractive index boundary;
   said optical fiber having said second refractive index, wherein said second refractive index is greater than said first refractive index; and
   a stimulating light;
   wherein, when an angle of incident of said fluorescence emission on said refractive index boundary is greater than a critical angle ($\theta_c$), said fluorescence emission coupled into said optical fiber is totally internally reflected upon application of the stimulating light.

4. An optical structure for metal-enhanced fluorescence sensing according to claim 1, wherein said conductive external coating on said optical fiber is a semi-transparent metal.

5. An optical structure for metal-enhanced fluorescence sensing according to claim 1, wherein said conductive external coating on said optical fiber comprises a noble metal.

6. An optical structure for metal-enhanced fluorescence sensing, comprising:
   an optical fiber having a conductive external coating;
   fluorophores disposed adjacent to said conductive external coating, wherein said conductive external coating on said optical fiber comprises metallic islands;
   a detector disposed at one end of said optical fiber;
   wherein fluorescence emissions of said fluorophores are coupled into said conductive external coating and into said optical fiber via application of surface plasmon excitation, and the fluorescence emissions are detected by the detector.

7. A method of metal-enhanced fluorescence sensing, comprising:
   applying a conductive coating to a surface of an optical fiber, wherein said conductive coating on said optical fiber comprises colloid spheres;
   introducing a solution containing analytes to said conductive coating;
   employing surface plasmon excitation to cause an excitation of fluorophores adjacent to said conductive coating;
   coupling said fluorescence emissions of said fluorophores into said conductive coating and into said optical fiber, and wherein said fluorescence emissions are detected by a detector.

8. A method of metal-enhanced fluorescence sensing according to claim 7, wherein said fluorescence emissions are totally internally reflected within said optical fiber in a direction towards the detector.

9. A method of metal-enhanced fluorescence sensing according to claim 7, wherein said conductive coating on said optical fiber is a semi-transparent metal.

10. A method of metal-enhanced fluorescence sensing according to claim 7, wherein said conductive coating on said optical fiber comprises a noble metal.

11. A method of metal-enhanced fluorescence sensing according to claim 8 comprising:

applying a conductive coating to a surface of an optical fiber, wherein said conductive coating on said optical fiber comprises metallic islands;

introducing a solution containing analytes to said conductive coating;

employing surface plasmon excitation to cause an excitation of fluorophores adjacent to said conductive coating;

coupling said fluorescence emissions of said fluorophores into said conductive coating and into said optical fiber, and the fluorescence emissions are detected by a detector.

* * * * *